US010571444B2

(12) United States Patent
Chokshi et al.

(10) Patent No.: US 10,571,444 B2
(45) Date of Patent: Feb. 25, 2020

(54) PROVIDING DATA TO A DISTRIBUTED BLOCKCHAIN NETWORK

(71) Applicant: INTERNATIONAL BUSINESS MACHINES CORPORATION, Armonk, NY (US)

(72) Inventors: Risham Y. Chokshi, North Brunswick, NJ (US); Autumn Good, Austin, TX (US); William Livesey, Seattle, WA (US); Andie Schroeder, Alston, MA (US)

(73) Assignee: INTERNATIONAL BUSINESS MACHINES CORPORATION, Armonk, NY (US)

(*) Notice: Subject to any disclaimer, the term of this patent is extended or adjusted under 35 U.S.C. 154(b) by 124 days.

(21) Appl. No.: 15/499,432

(22) Filed: Apr. 27, 2017

(65) Prior Publication Data

US 2018/0313797 A1    Nov. 1, 2018

(51) Int. Cl.
*G01N 33/00* (2006.01)
*G01D 9/00* (2006.01)
*G06F 21/78* (2013.01)

(52) U.S. Cl.
CPC ........... *G01N 33/004* (2013.01); *G01D 9/005* (2013.01); *G06F 21/78* (2013.01); *Y02P 90/845* (2015.11)

(58) Field of Classification Search
USPC ........................................................ 702/24
See application file for complete search history.

(56) References Cited

U.S. PATENT DOCUMENTS

| 7,853,436 | B2 | 12/2010 | McConnell et al. |
| 7,966,250 | B2 | 6/2011 | Constantz et al. |
| 2005/0273358 | A1* | 12/2005 | Zimmerman .......... G06Q 10/04 705/308 |
| 2006/0224410 | A1 | 10/2006 | Kimoto et al. |
| 2009/0056413 | A1* | 3/2009 | Rao .......................... F02C 9/28 73/23.31 |
| 2011/0087578 | A1 | 4/2011 | Finck et al. |
| 2011/0093321 | A1 | 4/2011 | Streetman |

(Continued)

OTHER PUBLICATIONS

Purohit et al.; Ttl: Non-stationarystochastic inventory lot-sizing with emission and service level constraints in a crabon cap-and-trade system; Publication Ttl: Journal of Cleaner Production, vol. 113, pp. 654-661; 2016; Publisher: Elsevier Sci Ltd.; Country of Publication: UK; ISSN: 0959-6526; Database: SciSearch.

*Primary Examiner* — Paul D Lee
(74) *Attorney, Agent, or Firm* — Conley Rose, P.C.

(57) ABSTRACT

A computer program product for providing data to a distributed blockchain database includes a computer readable storage medium having program instructions embodied therewith. The program instructions are executable by a computer to cause the computer to receive sensor data from a first sensor unit at a first location, receive additional data corresponding to a first parameter at the first location and forecast data corresponding to the first parameter at the first location, convert the sensor data into a standardized format, generate predicted future sensor data based on a comparison between the additional data, the sensor data, and the forecast data, write the sensor data, the additional data, and predicted future sensor data into a ledger. and submit the ledger to a distributed blockchain database.

20 Claims, 6 Drawing Sheets

(56) References Cited

U.S. PATENT DOCUMENTS

| | | | |
|---|---|---|---|
| 2012/0022700 A1* | 1/2012 | Drees | G05B 15/02 |
| | | | 700/276 |
| 2012/0083933 A1* | 4/2012 | Subbu | G06N 3/02 |
| | | | 700/291 |
| 2012/0095897 A1 | 4/2012 | Barrow | |
| 2015/0185194 A1 | 7/2015 | Prince et al. | |
| 2017/0013047 A1* | 1/2017 | Hubbard | H04L 67/20 |
| 2017/0103468 A1* | 4/2017 | Orsini | G06Q 40/12 |
| 2017/0358041 A1* | 12/2017 | Forbes, Jr. | H02J 13/001 |

* cited by examiner

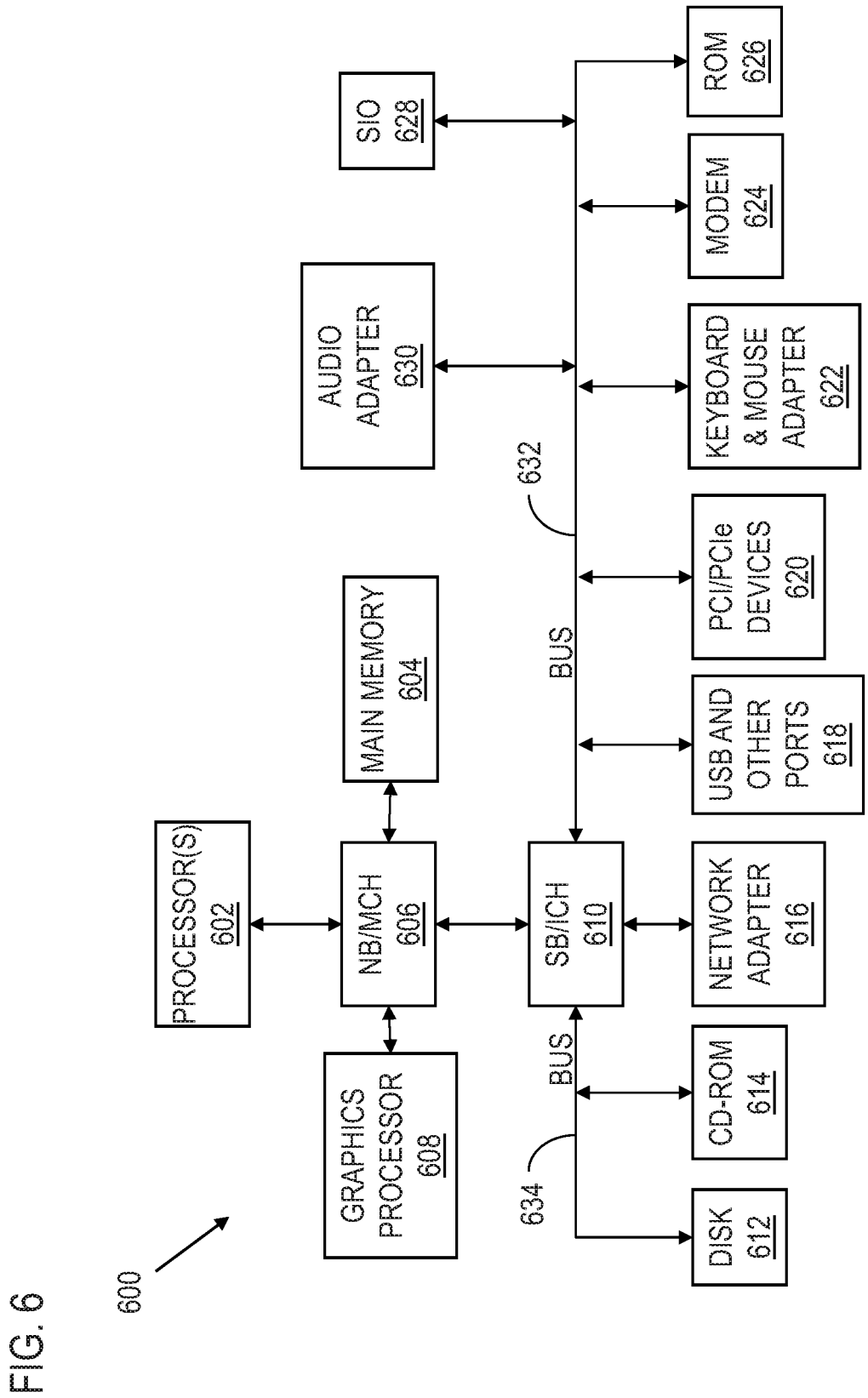

PROVIDING DATA TO A DISTRIBUTED BLOCKCHAIN NETWORK

STATEMENT REGARDING FEDERALLY SPONSORED RESEARCH OR DEVELOPMENT

N/A

STATEMENT REGARDING PRIOR DISCLOSURES BY THE INVENTOR OR A JOINT INVENTOR

N/A

BACKGROUND

The present disclosure relates to monitoring environmental parameters and, in some embodiments, trading environmental parameter allowances, and more specifically, to methods and systems for collecting, analyzing, acquiring and storing environmental parameter data in a distributed database that maintains a growing list of ordered records.

Carbon trading markets provide a financial incentive to reduce carbon emissions. For example, companies may be allowed a certain amount of carbon dioxide (a threshold limit) that they may emit over the course of a specific period of time. Companies emitting more carbon dioxide than the threshold limit may purchase a right to emit additional carbon from another company whose carbon emission allowance is then reduced by the amount purchased. Thus, the total amount of carbon emission allocations remains the same. However, these markets can be fragmented and disparate, which may lead to suboptimal carbon trading. For example, lack of proper standards for carbon emission measuring techniques leads to a drop in consumer confidence which further results in a suboptimal performance of the carbon trading market. Additionally, the carbon trading market relies on carbon emission data that may be prone to error. For example, one currently used carbon emission calculation process utilizes a number of intermediaries between carbon allocation buyer and seller which may lead to inaccuracies.

SUMMARY

In an embodiment, a system/apparatus is provided. The system/apparatus comprises a computing system configured to receive sensor data from a first sensor unit, receive weather data of a first location of the first sensor unit, convert the sensor data into a standardized form, write the sensor data and weather data into a ledger and submit the ledger to a distributed block chain database.

In a further embodiment, a computer program product including a computer readable storage medium encoded with program instructions is provided. The program instructions are executable by a computer to cause the computer to perform various ones of, and various combinations of the operations described above with respect to embodiments of a method.

BRIEF DESCRIPTION OF THE DRAWINGS

FIG. 6 shows an illustrative block diagram of an example data processing system that can be applied to implement embodiments of the present disclosure.

DETAILED DESCRIPTION

The usefulness of emission trading markets is tied to the optimal measurement of emissions of an environmental parameter (e.g., carbon dioxide). However, emission trading markets rely on a system that is fragmented and disparate. Further, emissions data is prone to error because conventional systems are based on human estimates and calculations. For example, carbon dioxide emitters measure their own carbon dioxide emissions, then have the measured emission data verified by a trusted third party. The emitters then may use the verified carbon dioxide emission data for carbon trading using a separate trading market. Therefore, it is desirable to develop a trusted system which automatically measures emissions and stores emissions data in a distributed database (e.g., a blockchain database). The stored emission data then may be utilized for trading emission allowances. In accordance with various examples, a system may be provided to measure environmental parameter emissions using sensors (e.g., internet of things (IoT) sensors) and store the emissions data in a blockchain database. Users may utilize the stored emission data from the blockchain database to perform emission allowance trading. In accordance with other examples, a system may utilize the emissions data and compare the data with past weather information from when the data was generated to predict future emissions based on weather forecasts.

The embodiments described herein include a plurality of computer systems, each of which may store a blockchain database. The computer systems may be connected to each other through a network, thus, a distributed blockchain database is formed. The disclosed embodiments further include a plurality of sensor units placed at a plurality of different locations, each sensor measuring an environmental parameter, such as carbon dioxide emissions. In an embodiment, the environmental parameter is measured and transmitted by the sensor unit to a central-computing system. The environmental parameter data is added to the blockchain database which is replicated by all the computer systems. Because the data stored in a blockchain database is exceptionally difficult to alter once committed to the blockchain, the system and methods described herein provide a robust trail of environmental parameter data and other related transactional records. In some embodiments, the measured emission data may exceed a threshold value resulting in acquiring one or more additional environmental emission allowances.

Figure 1:
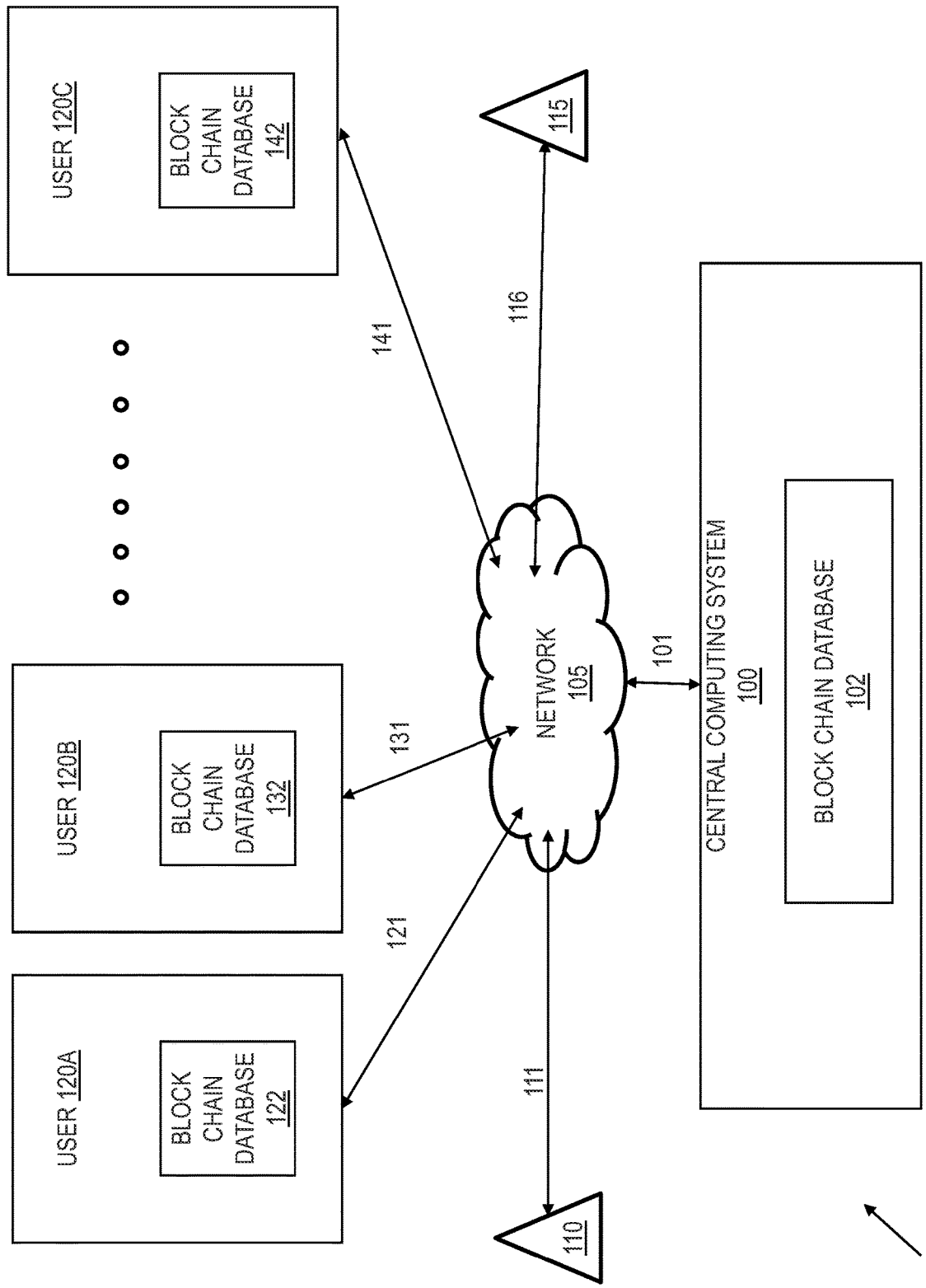
FIG. 1 shows an illustrative diagram of a system that collects and stores environmental parameter data in accordance with various embodiments.

FIG. 1 shows an illustrative diagram of a system 50 that collects, converts, stores, analyzes, and acquires data in accordance with various embodiments. The system 50 includes a plurality of computer systems such as central-computing system 100 and Users 120A-N. The system 50 further includes a network 105 and sensor units 110, 115 which may be placed at different geographic locations. In an embodiment, the sensor units 110, 115 are IoT sensors, such that the sensor units 110, 115 may be any physical device that includes embedded electronics that allow the sensor units 110, 115 to sense emissions at the location that the sensor unit is located. The computing system 100 can be configured to receive sensor data (i.e., emission data) from the sensor units 110, 115. For example, the computing system 100 may receive and store carbon dioxide emission data sensed by sensors units 110, 115 from multiple geographic locations. More particularly, the sensor unit 110 may sense carbon dioxide emissions at one geographic location (e.g., a smoke stack in Pittsburgh, Pa.), while sensor unit 115 may sense carbon dioxide emissions data at a second geographic location (e.g., a smoke stack in Philadelphia, Pa.). The emission data detected by sensors units 110, 115 then may be transmitted to computing system 100, in some embodiments, through the network 105. Thus, the sensor units 110, 115 have transmission capabilities to enable the sensor to transmit the sensor data to the computing system 100. Further, the computer systems (central computing system 100 and Users 120A-N) may form a distributed network which maintains and builds upon a blockchain database. For example, computing system 100 and each of the uses 120A-N may maintain a copy of the blockchain in their respective blockchain database 102, 122, 132, and 142

As discussed above, in some embodiments, there may be a plurality of sensor units at a plurality of different locations transmitting sensor data to the computing system 100. For example, the sensor units may be placed at different locations by a trusted third party (such as a government organization) where the sensor units measure some data (such as carbon dioxide emission data). The placement of the sensor units 110, 115 is illustrative and is not intended to state or imply any limitation with regard to the type of system with which various embodiments may be implemented. Many modifications to the example placements of the sensor units 110, 115 and the computing system 100 may be implemented in various embodiments.

In some embodiments, the computing system 100 may include one or more processors and one or more memories (not shown), and/or a distributed blockchain database 102. In some embodiments, the computing system 100 can be a cognitive computing system that ingests and analyzes data from multiple sources. In some illustrative embodiments, the computing system 100 may be the IBM Watson™ system available from International Business Machines Corporation of Armonk, N.Y.

The sensor units 110, 115 may include a processor, a memory, one or more sensors, a communication interface and a location sensor (such as a Global Positioning System (GPS)). The sensors (not shown) in the sensor units may measure a certain quantity of an environmental parameter such as carbon dioxide. For example, the sensor unit 110, 115 can be placed at a location of direct carbon dioxide emission such as a chimney of a coal plant where the sensors may measure carbon dioxide emission from the coal plant. Measuring carbon dioxide emission may include: detecting and measuring carbon dioxide emission data (in parts per million) for a first time period using the sensors and transmitting the measured carbon dioxide emission data to the computing system 100 through a communication link (such as 111, 116, 101) over network 105 (for example, the internet). The sensor unit may also calculate the cumulative carbon dioxide emission data which may be the total carbon emission data received in a certain time interval which may be a longer time interval than the first time interval.

In some embodiments, the Users 120A-N can be one or more computer systems employed by emitters (such as fossil burning plants emitting carbon dioxide, etc.). The Users 120A-N may include one or more processors and one or more memories (not shown). A distributed blockchain database 122, 132, 142 may be stored in the one or more memories and may include an operator. The Users 120A-N may include any other computing device elements generally known in the art including buses, storage devices, communication interfaces, and the like. The Users 120A-N may further be equipped to analyze the emission data received through the blockchain database. The Users 120A-N may also participate in emission allowance trading with other users in the distributed blockchain network or through any other network. For example, user 120A may receive a notification related to carbon emission data exceeding a threshold value. This threshold value may correspond or be based on the emission allowances for a particular user. For example, the user 120A may have an allowance to emit 100 tons of carbon dioxide per year. The user 120A may transmit to the computer system 100 that it would like to set a threshold value of 90 tons of carbon dioxide. Thus, if the carbon emission data for the current year exceeds 90 tons of carbon dioxide, the computer system 100 may generate and transmit a notification to user 120A that the threshold value (i.e., 90 tons of carbon dioxide) has been exceeded. This may prompt the user 120A to acquire additional carbon allowances from another User, such as user 120B using a carbon trading market.

As discussed above, measuring emissions may include measuring an environmental parameter emissions (for example, in parts per million) for any time period. In some embodiments, the time period for which the emissions are measured can be preset or in other embodiments, the time period can be programmable. For example, the timing sequence can be a fixed timing waveform such that the sensors units 110, 115 measure the environmental parameter (e.g., carbon dioxide) when the sequence is at a higher logic and transmit the measured emission data when the sequence is at a lower logic. The fixed timing sequence is illustrative and is not intended to state or imply any limitation with regard to the type of timing sequence with which various embodiments may be implemented, In some embodiments, the sensor units 110, 115 can be programmed to alter the timing sequence. In some embodiments, the timing sequence may be programmed through the communication links 111, 116. For example, the sensor units 110, 115 may be programmed to measure the environmental parameter more frequently in an event the sensors measure a higher than average amount of the environmental parameter. In some embodiments, the timings sequence can be altered by the trusted third party through the communication interface in the sensor unit. In other embodiments, the timing sequence may be altered by an emitter through their respective users (i.e. Users 120A-N) via a communication interface in the sensor unit.

Figure 2:
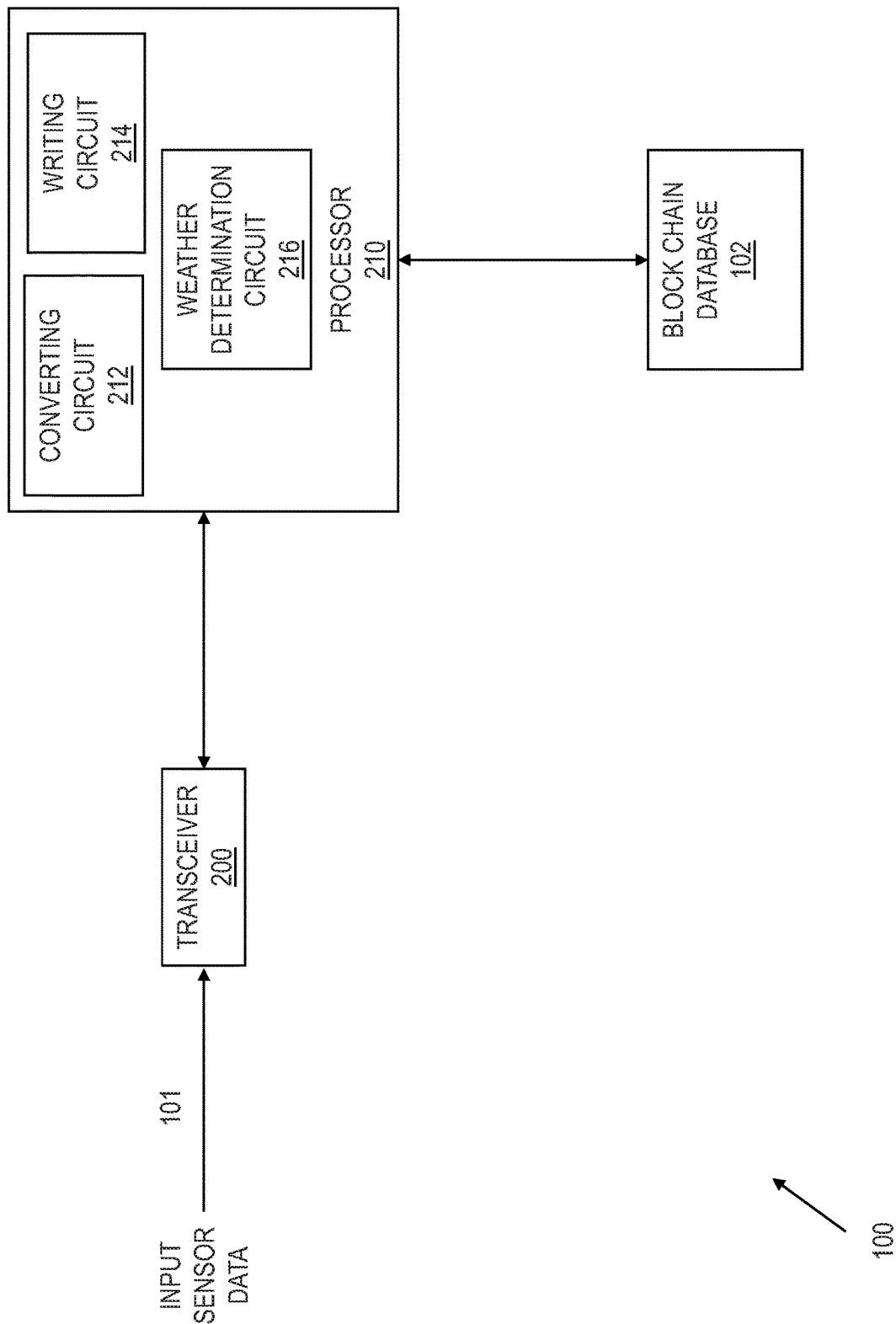
FIG. 2 shows an illustrative block diagram of an example computing system for processing environmental parameters, in accordance with various embodiments.

FIG. 2 shows an illustrative block diagram of computing system 100, in accordance with various embodiments. The computing system 100 may include a transceiver 200, a processor 210, and a blockchain database 102. The processor 210 may further comprise a converting circuit 212, a writing circuit 214, and weather determination circuit 216.

In some embodiments, the transceiver 200 is configured to receive data, such as sensor data through the communication link 101. For example, the transceiver 200 may receive carbon emission data transmitted by the sensor units 110, 115. In an example embodiment, the computing system 100 may be configured to request and receive weather data of a geographic location of a sensor unit through the weather determination circuit 216. For example, the sensor unit 110 may be placed in a coal burning power plant in a first geographic location (e.g., a coal burning plant in Texas) and the sensor unit 115 may be placed in another fossil fuel power plant located in a second geographic location (e.g., a smoke stack in Colorado). The weather determination circuit 216 may request weather data of each of the first and second location through a trusted third party weather server (such as a commercial weather service, government weather service etc.) and/or receive direct weather reports from the sensor units 110, 115 which, in some embodiments, may, in addition to sensing emissions, may sense weather data as well. In some embodiments, the weather determination circuit 216 may request the weather data at a fixed rate (for example, every hour or every day) or at a programmable rate.

Upon receiving the environmental parameter data from the sensor units 110, 115, a converting circuit 212 may process and convert the data into a standardized form by performing a mathematical function on the received data. For example, carbon emission data may be measured in parts per million by the sensor unit 110 and may be converted to a standardized form of metric ton per year. This transformation may require the converting circuit 212 to apply the mathematical function to the received emission data resulting in converted emission data.

Following the conversion to the standardized form and receiving weather data of each location of the sensor units, the writing circuit 214 may write the environmental parameter data and the weather data into a ledger to be incorporated into a blockchain which is stored in blockchain databases 102, 122, 132, 142. The writing circuit 214 may also write transactional data records related to emission allowance values and data related to a request for additional emission allowance in the ledger. The emission allowance value may be the allowed emissions per unit of time (e.g. year) for a specific emitter. The emission allowance value can be transmitted to the central-computing system 100 by the user 120A-N associated with the specific emission allowance value. For example, the emission allowance value for carbon emissions for user 120A may be provided by user 120A. In other embodiments, the emission allowance value can be preset by a trusted third party (such as an environmental protection agency, government, etc.). The writing circuit 214 may also write into the ledger cumulative converted emission data which may be the total converted environmental parameter emission data received for each user 120A-N.

The writing process may be instantaneous or may occur with a writing timing sequence. For example, for the instantaneous writing process, the emission data and the weather data may be written into the ledger instantaneously or immediately following the conversion. In other embodiments, converted emission data may be stored in memory (not shown) and written into the ledger as directed by a writing timing sequence. For example, the writing timing sequence may have a writing period and a non-writing period. During the writing period the writing circuit 214 may be directed to write converted emission data and the collected weather data into the ledger, and during the non-writing period, the writing circuit 214 may not write data into the ledger. The writing timing sequence of the writing circuit 214 is illustrative and is not intended to state or imply any limitation with regard to the type of system with which various embodiments may be implemented. Many modifications to the example writing timing sequence of the writing circuit 214 may be implemented in various embodiments.

The ledger may be submitted to the distributed blockchain database (102, 122, 132, 142) following writing data into the ledger. For example, the distributed blockchain database may receive a submit request and the computer systems scoring the distributed blockchain database (such as 100, 120, 130, 140) initiate attempts to mine or unlock a new block in the block chain. The computer system that successfully mines a new block attaches the ledger in the new block and propagates the new block to the distributed blockchain network. Therefore, all the computer systems (such as 100, 120, 130, and 140) scoring the distributed blockchain database 102, 122, 132, and 142 receive a copy of the ledger. As discussed above, the ledger may include transactional data, emission data from each sensor unit 110, 115, weather data from each location of the sensor units 110, 115, and may also contain the cumulative emission data for each user 120A-N.

Figure 3:
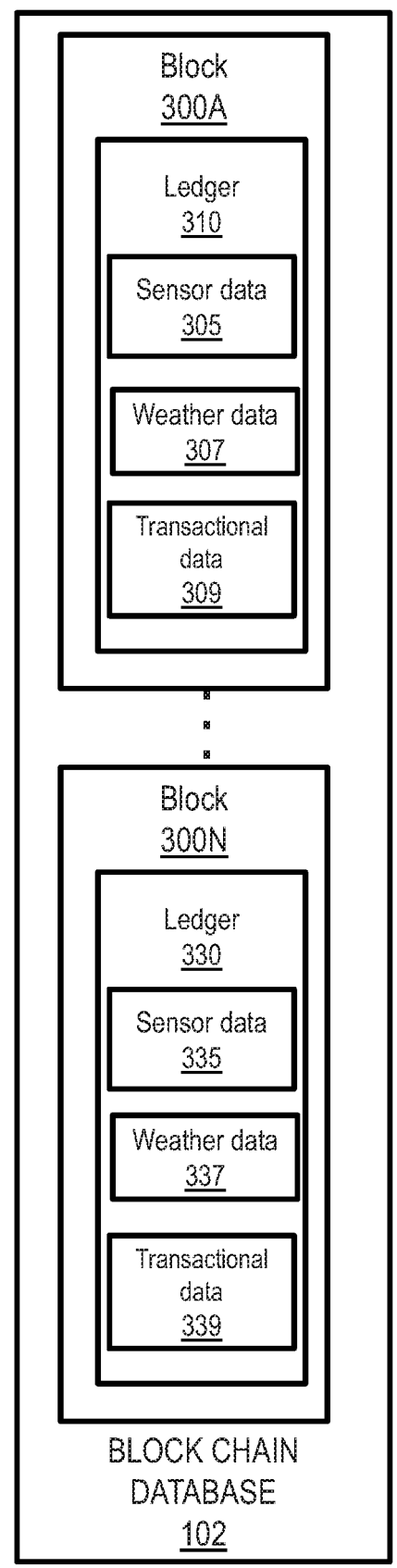
FIG. 3 shows a block diagram of an example block chain database, in accordance with various embodiments.

FIG. 3 shows a block diagram of an example blockchain database (such as 102, 122, 132, 142), in accordance with various embodiments. FIG. 3 shows an illustrative architecture of blockchain database 102, although the architecture can apply to any other or all of the other blockchain databases disclosed herein. Blockchain database 102 may include one or more blocks, blocks 300A-N as indicated by the ellipses. In each block, a ledger containing converted emission data, weather data, cumulative converted emission data, environmental emission allowance values and other transactional records are stored. For example, ledger 310, which comprises sensor data 305 (e.g., converted emission data), weather data 307, and transactional data 309 is stored in the block 300A. Similarly, ledger 330 comprises sensor data 335 (e.g., converted carbon data), weather data 337, and transactional data 339 which is stored in the block 300N. Therefore, each of blocks 300A-N is a group of ledgers containing records. In some embodiments, each block is chained or contains information that relates it to the previous block in the blockchain database.

Each of computer systems 100, 120, 130, 140 from FIG. 1 may be configured to add a block, such as block 300A, to the distributed blockchain database 102, 122, 132, 142. In this example, block 300A already exists in the blockchain database 102. Mining or adding a block is the process of adding additional blocks, such as block 300N to the distributed blockchain database 102, 122, 132, 142. In order to successfully mine the block 300N, one of computer systems 100, 120, 130, 140, or any other computing system associated with the blockchain network, may solve an arbitrary problem and provide its solution to the remaining computer systems in the network. In some embodiments, the arbitrary problem requires one of computer systems 100, 120, 130, 140, or any other computing system associated with the blockchain network, to determine an arbitrary value, such that when hashed, the block content along with the arbitrary value is added to the blockchain.

Figure 4:
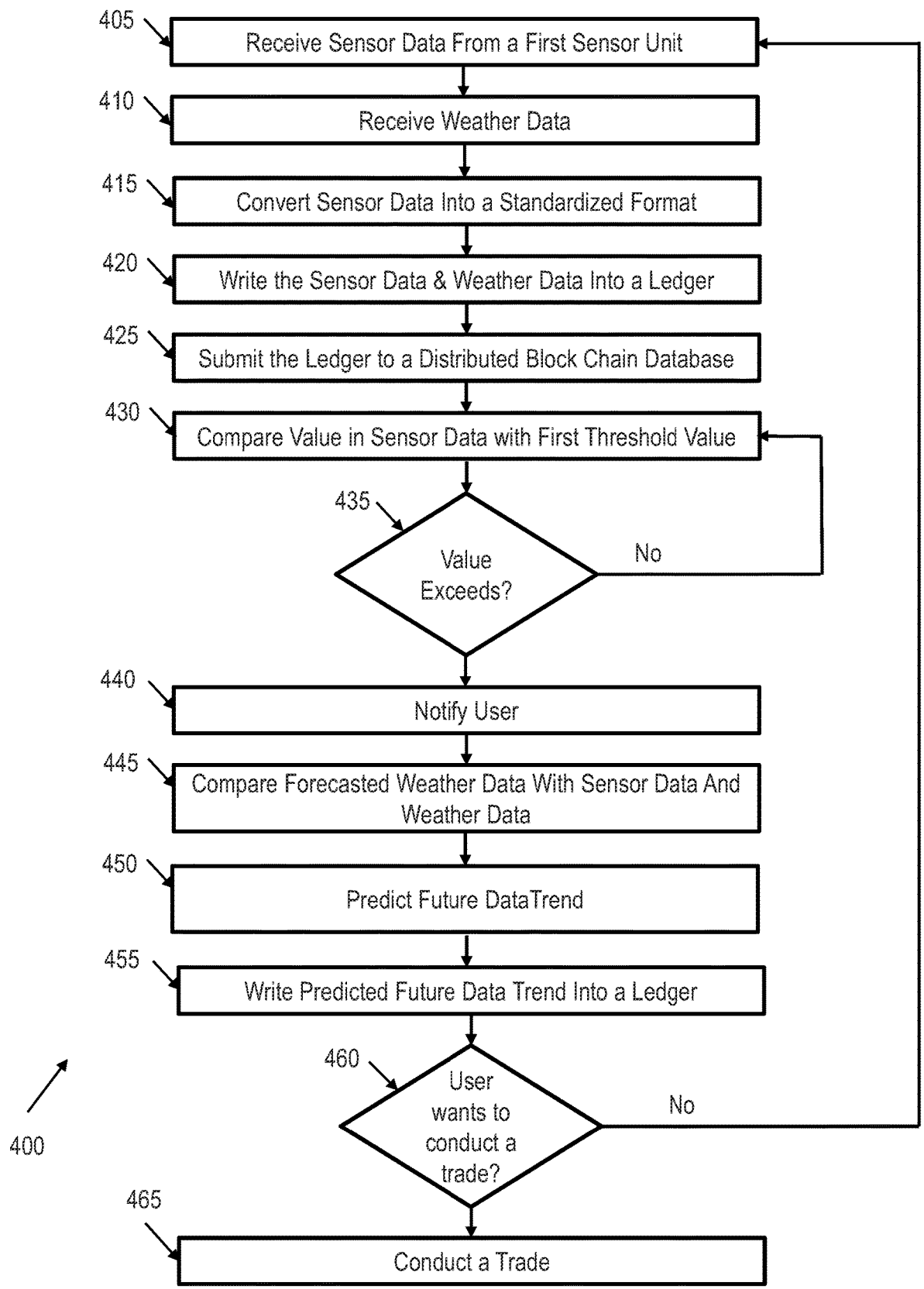
FIG. 4 shows a flow diagram illustrating aspects of operations that may be performed to acquire environmental emission allowances, in accordance with various embodiments.

FIG. 4 shows a flow diagram illustrating aspects of operations that may be performed to acquire additional environmental emission allowance in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of the method 400 may be provided by instructions executed by the computing system 100.

The method 400 begins in block 405 with receiving sensor data from a first sensor unit. For example, the sensor data may comprise any type of environmental parameter emission data (e.g., carbon dioxide emission data) measured by the first sensor unit 110 at a first location (i.e., the location of the sensor unit 110). In block 410, the method 400 continues with receiving weather data of the first location. For example, the weather determination circuit 216 may request weather data of a first geographic location (e.g., Pittsburgh) of the sensor unit 110 through a trusted third party weather server (e.g. government weather database). In another example, the sensor unit 110 may sense the weather conditions and transmit the sensed weather conditions as data to the computer system 100.

The method 400 continues in block 415 with converting the sensor data into a standardized format. For example, the received emission data may be different than a standardized unit based on a consensus of different parties. In an example embodiment, the received emission data may be in parts per million whereas the consensus unit for the emission data may be metric tons per year. Therefore, to maintain a uniform system of engagement, the emission data is converted into the standardized format (in this case, metric tons per year). Following the conversion process, the converted emission data may be stored in a local memory of the computing system 100 where the computing system 100 may also count and register a cumulative converted carbon data in the local memory.

The method 400 further continues in block 420 with writing the sensor data and writing weather data of the location of the sensor unit into a ledger. In some embodiments, the block 420 may also write environmental emission allowance data, cumulative converted emission data, and transactional records related to the emission allowance into the ledger.

The writing may be instantaneous or occur in accordance with a writing timing sequence. For example, the instantaneous writing sequence may direct the converted emission data, the weather data, and the cumulative converted emission data to be written into the ledger instantaneously following the conversion. In some embodiments, the converted emission data may be first stored in memory and then written into a ledger as directed by a writing timing sequence. The writing timing sequence may have a writing period and a non-writing period, where during the writing period the writing circuit 214 may be directed to write the converted emission data and weather data into the ledger and during the non-writing period, the writing circuit 214 may not write any data into the ledger.

The method 400 continues in block 430 with comparing the cumulative converted emission data with a first threshold value. The method 400 further continues in block 435 where a determination is made as to whether the cumulative converted emission data exceeds the first threshold value. For example, over time, with continuous carbon dioxide emission, the received carbon emission data adds up and the cumulative converted carbon dioxide emission data may reach 90% of the allowance value. In some embodiments, the first threshold value may be preset by a user (such as one or more of Users 120A-N). As describe above, the emission allowance value set for each of the emitters may be received by the computer system 100 through a trusted third party (such as environmental protection agency etc.).

Once the cumulative converted emission data exceeds the first threshold, the computing system 100 notifies the corresponding user as described in block 440. In this example, the first threshold value is 90% of the carbon dioxide emission allowance value. Therefore, once the cumulative converted carbon dioxide emission data shows that 90% of the carbon dioxide emission allowance has been reached, the computing system 100 may generate and transmit the notification to the corresponding user.

In block 445, the method 400 continues with comparing forecasted weather data with the converted emission data determined in block 415 and the weather data determined in block 410 of the first location. For example, the processor 210 may gather the forecasted weather data through a trusted weather server and compare it to historically collected emissions data and the corresponding weather data. In block 450, the method 400 continues with predicting a future data trend. For example, using a computer program on such a large data set may provide insights over future trends in the emission data based on the weather. For example, if the temperature is 20 degrees Celsius (C) for one hour and the emission data shows 0.1 ton of carbon dioxide is emitted during that one hour, then the system may predict that whenever the temperature is 20 degrees C., the emissions rate will be 0.1 tons per hour. Therefore, if the forecasted weather shows 20 degrees C. for tomorrow for 6 hours, then the processing unit 210 may determine that for those 6 hours, 0.6 tons of carbon dioxide will be emitted.

The method 400 continues in block 455 with writing the predicted future trend of the emission data into a ledger which may be submitted to the distributed blockchain 425. After successfully mining a new block, the miner attaches the ledger in the new block and propagates the new block to the distributed blockchain network. Therefore, all the computer systems 100, 120, 130, and 140 storing the distributed blockchain database 102, 122, 132, and 142 receive a copy of the ledger which may contain the sensed emission data, the weather data, and/or the predicted future trend of the emission data.

The method 400 continues 460 in determining if the user wants to conduct a trade. As described above, the predicted future trend of the emission data propagates to all the computer systems which may include the Users 120A-N. For example, user 120A may receive the future trend of the emission data and may utilize this data to make the decision to trade. For example, the user 120A may determine that based on the future emission data, the user's emission allowances will be exceeded shortly; therefore, the user 120A may trade for additional emission allowances prior to exceeding the allowance. Thus, the trade may include a request to buy additional emission allowances. In block 465, the method 400 continues with conducting the trade. For example, user 120A may conduct the trade with user 120B and obtain the additional emission allowances.

Figure 5:
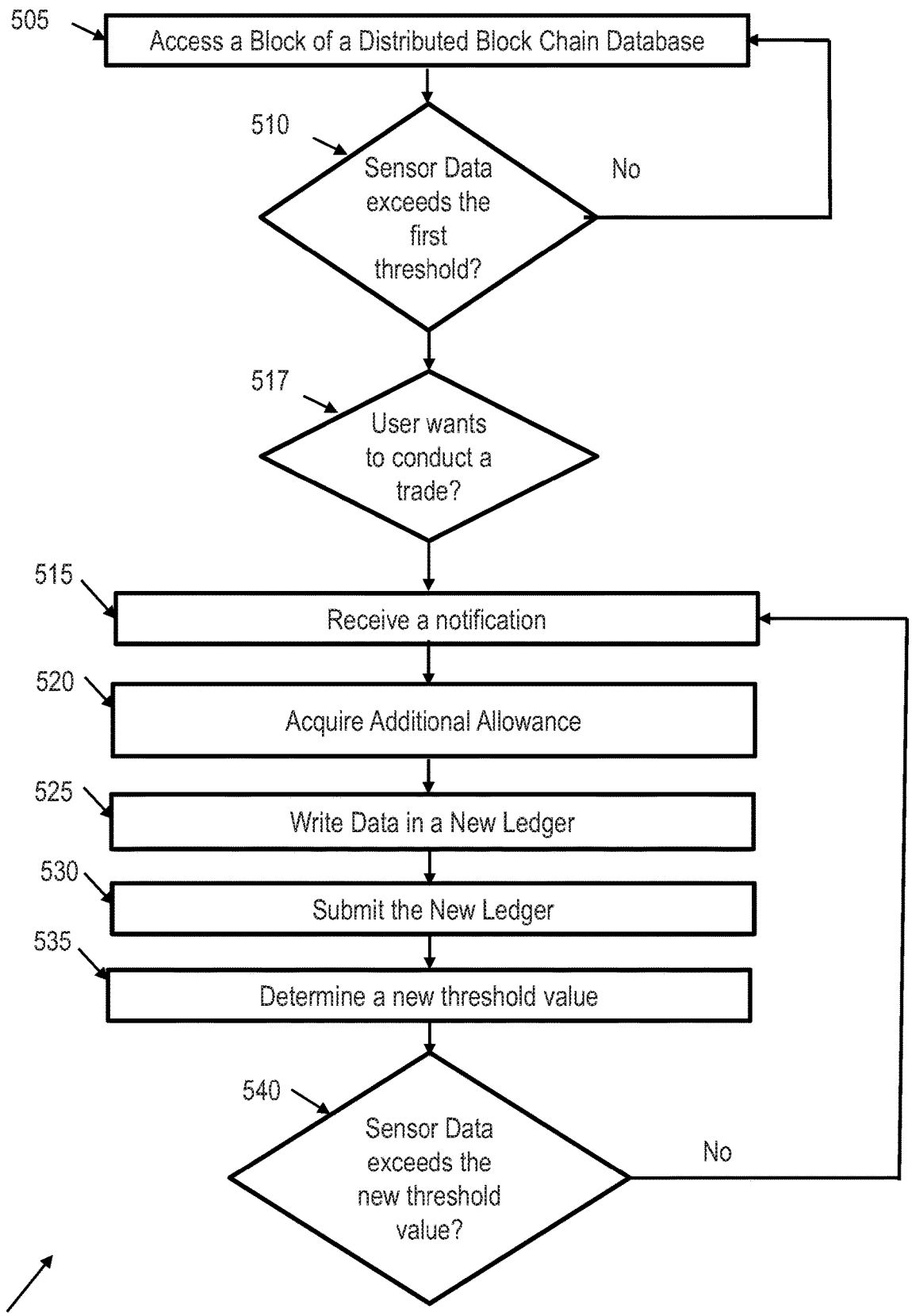
FIG. 5 shows a flow diagram illustrating aspects of operations that may be performed to acquire environmental emission allowances and submit a ledger to a block chain database, in accordance with various embodiments.

FIG. 5 shows a flow diagram illustrating aspects of operations that may be performed to acquire additional emission allowances and to submit a ledger to the distributed blockchain in accordance with various embodiments. Though depicted sequentially as a matter of convenience, at least some of the actions shown can be performed in a different order and/or performed in parallel. Additionally, some embodiments may perform only some of the actions shown. In some embodiments, at least some of the operations of the method 500 may be provided by instructions executed by computing systems 120, 130, 140.

The method 500 starts in block 505 with accessing a newest block from the distributed blockchain database. The newest block may include a ledger containing converted emission data, weather data, cumulative converted emission data, forecasted weather data, and/or a predicted future trend of the emission data. The method 500 continues in block 510 with determining if the cumulative converted emission data exceeds a first threshold value. The first threshold value may be user specific. For example, user 120A may have the first threshold preset at 90% of its emission allowance value. Similarly, user 120B may have a first threshold value set at 60% of its emission allowance value. Thus, in block 515, if the cumulative converted emission data exceeds the first threshold value for any of the particular users, a notification may be received by the corresponding user. For example, after accessing the newest block from the distributed blockchain database, user 120A may receive a notification, in some embodiments in the ledger of the newest block, if the cumulative converted emission data exceeds the first threshold value.

The method 500 continues in block 517 with determining if the user wants to conduct a trade. For example, user A may analyze the predicted future emission data to determine if the user A needs to acquire additional emission allowance. The method 500 continues in block 520 with acquiring additional allowances in response to the result of the determination of block 517. For example, user 120A may acquire additional allowance thereby increasing the total emission allowance for that user. The user 120A may further write (as shown in block 525) the additionally acquired allowance data and/or the total allowance data in a new ledger and submit (as shown in block 530) a transaction showing the acquired allowances and/or the total allowances to the distributed blockchain database. After successfully mining a new block, the miner may attach the new ledger in the new block and propagate the new block to the distributed blockchain network. Therefore, all the computer systems 100, 120, 130, and 140 of the distributed blockchain database receive a copy of the ledger.

The method 500 further continues in block 535 with a user 120A determining a second threshold value and further in block 540 determines if the cumulative converted emission data exceeds the second threshold value.

FIG. 6 is a block diagram of an example data processing system in which aspects of the illustrative embodiments may be implemented. Data processing system 600 is an example of a computer that can be applied to implement the computing system 100 or any of the user systems 120A-N in FIG. 1 and FIG. 2, in which computer usable code or instructions implementing the processes for illustrative embodiments of the present invention may be located. In one illustrative embodiment, FIG. 6 represents a computing device that implements the computing system 100 augmented to include the additional mechanisms of the illustrative embodiments described hereafter.

In the depicted example, data processing system 600 employs a hub architecture including north bridge and memory controller hub (NB/MCH) 606 and south bridge and input/output (I/O) controller hub (SB/ICH) 610. Processor(s) 602, main memory 604, and graphics processor 608 are connected to NB/MCH 606. Graphics processor 608 may be connected to NB/MCH 606 through an accelerated graphics port (AGP).

In the depicted example, local area network (LAN) adapter 616 connects to SB/ICH 610. Audio adapter 630, keyboard and mouse adapter 622, modem 624, read only memory (ROM) 626, hard disk drive (HDD) 612, compact disk read-only memory (CD-ROM) drive 614, universal serial bus (USB) ports and other communication ports 618, and peripheral component interconnect/peripheral component interconnect express (PCI/PCIe) devices 620 connect to SB/ICH 610 through bus 632 and bus 634. PCI/PCIe devices may include, for example, Ethernet adapters, add-in cards, and personal computer (PC) cards for notebook computers. PCI uses a card bus controller, while PCIe does not. ROM 626 may be, for example, a flash basic input/output system (BIOS).

HDD 612 and CD-ROM drive 614 connect to SB/ICH 610 through bus 634. HDD 612 and CD-ROM drive 614 may use, for example, an integrated drive electronics (IDE) or serial advanced technology attachment (SATA) interface. Super I/O (SIO) device 628 may be connected to SB/ICH 610.

An operating system runs on processor(s) 602. The operating system coordinates and provides control of various components within the data processing system 600 in FIG. 6. In some embodiments, the operating system may be a commercially available operating system such as Microsoft® Windows 10®. An object-oriented programming system, such as the Java™ programming system, may run in conjunction with the operating system and provides calls to the operating system from Java™ programs or applications executing on data processing system 600.

In some embodiments, data processing system 600 may be, for example, an IBM® eServer™ System P® computer system, running the Advanced Interactive Executive (AIX®) operating system or the LINUX® operating system. Data processing system 600 may be a symmetric multiprocessor (SMP) system including a plurality of processors 602. Alternatively, a single processor system may be employed.

Instructions for the operating system, the object-oriented programming system, and applications or programs are located on storage devices, such as HDD 612, and may be loaded into main memory 604 for execution by processor(s) 602. The processes for illustrative embodiments of the present invention may be performed by processor(s) 602 using computer usable program code, which may be located in a memory such as, for example, main memory 604, ROM 626, or in one or more peripheral devices 612 and 614, for example.

A bus system, such as bus 632 or bus 634 as shown in FIG. 6, may include one or more buses. The bus system may be implemented using any type of communication fabric or architecture that provides for a transfer of data between different components or devices attached to the fabric or architecture. A communication unit, such as modem 624 or LAN adapter 616 of FIG. 6, may include one or more devices used to transmit and receive data. A memory may be, for example, main memory 604, ROM 626, or a cache such as found in NB/MCH 606 in FIG. 6.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or eternal storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:
1. A method for predictive environmental emissions allowances trading, the method comprising:
receiving sensor data from a first environmental emissions sensor at a first location;
receiving additional data corresponding to a first parameter at the first location and forecast data corresponding to the first parameter at the first location;
converting the sensor data into a standardized format;

generating predicted future sensor data based on a comparison between the additional data, the sensor data, and the forecast data;
writing the sensor data, the additional data, and the predicted future sensor data into a ledger; and
submitting the ledger to a distributed blockchain database;
wherein the distributed blockchain database supports an environmental emissions allowances trade in a distributed computer network that maintains the distributed blockchain database.

2. The method of claim 1, further comprising receiving additional sensor data from a second environmental emissions sensor at a second location.

3. The method of claim 2, wherein the sensor data from the first environmental emissions sensor corresponds with carbon dioxide emissions at the first location, and wherein the additional sensor data from the second environmental emissions sensor corresponds with carbon dioxide emissions at the second location.

4. The method of claim 1, further comprising receiving blockchain timing instructions from a user that provides instructions of when to write into the ledger.

5. The method of claim 1, further comprising:
compare the sensor data with a first threshold value; and
in response to a determination that the sensor data includes a value that exceeds the first threshold value, sending a notification to a user.

6. The method of claim 1, further comprising:
comparing the sensor data with a first threshold value received from a user; and
in response to a determination that the sensor data includes a value that exceeds the first threshold value, acquiring an additional carbon dioxide emission allowance for a user.

7. The method of claim 1, wherein the forecast data corresponds to a forecast of the first parameter, wherein the first parameter is weather, and wherein the forecast of the first parameter is a weather forecast.

8. The method of claim 1, wherein the environmental emissions allowances trade includes a request to buy an emission allowance.

9. The method of claim 1, further comprising utilizing at least a portion of the distributed blockchain database including the predicted future sensor data to initiate the environmental emissions allowances trade.

10. The method of claim 1, further comprising generating the sensor data based on measurements of an environmental parameter, wherein a time between the measurements of the environmental parameter depends on an amount of the environmental parameter.

11. A system for predictive environmental emissions allowances trading, the system comprising:
at least one memory having at least one set of instructions therein, and
at least one processor in communication with the at least one memory, wherein the at least one processor is configured to execute the at least one set of instructions to:
receive sensor data from a first environmental emissions sensor at a first location;
receive additional data corresponding to a first parameter at the first location and forecast data corresponding to the first parameter at the first location;
convert the sensor data into a standardized format;
generate predicted future sensor data based on a comparison between the additional data, the sensor data, and the forecast data;
write the sensor data, the additional data, and the predicted future sensor data into a ledger; and
submit the ledger to a distributed blockchain database;
wherein the distributed blockchain database supports an environmental emissions allowances trade in a distributed computer network that maintains the distributed blockchain database.

12. The system of claim 11, wherein the at least one processor is further configured to execute the at least one set of instructions to receive additional sensor data from a second environmental emissions sensor at a second location.

13. The system of claim 12, wherein the sensor data from the first environmental emissions sensor corresponds with carbon dioxide emissions at the first location, and wherein the additional sensor data from the second environmental emissions sensor corresponds with carbon dioxide emissions at the second location.

14. The system of claim 11, wherein the at least one processor is further configured to execute the at least one set of instructions to:
compare the sensor data with a first threshold value; and
in response to a determination that the sensor data includes a value that exceeds the first threshold value, send a notification to a user.

15. The system of claim 11, wherein the at least one processor is further configured to execute the at least one set of instructions to:
compare the sensor data with a first threshold value received from a user; and
in response to a determination that the sensor data includes a value that exceeds the first threshold value, acquire an additional carbon dioxide emission allowance for a user.

16. The system of claim 11, wherein the forecast data corresponds to a forecast of the first parameter.

17. The system of claim 11, wherein the environmental emissions allowances trade includes a request to buy an emission allowance.

18. The system of claim 11, wherein the at least one processor is further configured to execute the at least one set of instructions to utilize at least a portion of the distributed blockchain database including the predicted future sensor data to initiate the environmental emissions allowances trade.

19. The system of claim 11, wherein the at least one processor is further configured to execute the at least one set of instructions to generate the sensor data based on measurements of an environmental parameter at a variable frequency, wherein the variable frequency depends on an amount of the environmental parameter.

20. A computer program product for predictive environmental emissions allowances trading, the computer program product comprising a computer readable storage medium having program instructions embodied therewith, the program instructions executable by a computer to cause the computer to:
receive sensor data from a first environmental emissions sensor at a first location;
receive additional data corresponding to a first parameter at the first location and forecast data corresponding to the first parameter at the first location;
convert the sensor data into a standardized format;
generate predicted future sensor data based on a comparison between the additional data, the sensor data, and the forecast data;
write the sensor data, the additional data, and the predicted future sensor data into a ledger; and submit the ledger to a distributed blockchain database;
wherein the distributed blockchain database supports an environmental emissions allowances trade in a distributed computer network that maintains the distributed blockchain database.

* * * * *